United States Patent
Leveen et al.

(10) Patent No.: US 6,575,967 B1
(45) Date of Patent: *Jun. 10, 2003

(54) METHOD AND SYSTEMS FOR VOLUMETRIC TISSUE ABLATION

(75) Inventors: Robert F. Leveen, Gainsville, FL (US); Randy Fox, Lincoln, NE (US)

(73) Assignee: The Board of Regents of the University of Nebraska, Lincoln, NE (US)

(*) Notice: Subject to any disclaimer, the term of this patent is extended or adjusted under 35 U.S.C. 154(b) by 0 days.

This patent is subject to a terminal disclaimer.

(21) Appl. No.: 09/501,338

(22) Filed: Feb. 9, 2000

Related U.S. Application Data

(63) Continuation-in-part of application No. 08/559,072, filed on Nov. 16, 1995, which is a continuation of application No. 08/410,344, filed on Mar. 24, 1995, now Pat. No. 5,868,740.

(51) Int. Cl.[7] .............................................. A61B 18/14
(52) U.S. Cl. ............................. 606/41; 606/49; 606/50; 607/99; 607/113; 607/116
(58) Field of Search ........................... 606/41, 49, 50; 607/98, 99, 113, 116, 128

(56) References Cited

U.S. PATENT DOCUMENTS

| | | |
|---|---|---|
| 164,183 A | 6/1875 | Kidder |
| 1,814,791 A | 7/1931 | Ende |
| 1,908,583 A | 5/1933 | Wappler |
| 1,943,543 A | 1/1934 | McFadden |
| 2,004,559 A | 6/1935 | Wappler et al. |
| 2,022,065 A | 11/1935 | Wappler |
| 2,056,377 A | 10/1936 | Wappler |
| 3,460,539 A | 8/1969 | Anhalt |
| 3,645,265 A | 2/1972 | Majzlin |
| 3,858,586 A | 1/1975 | Lessen |
| 4,003,380 A | 1/1977 | Wien |
| 4,005,714 A | 2/1977 | Hiltebrandt |

(List continued on next page.)

FOREIGN PATENT DOCUMENTS

| | | |
|---|---|---|
| DE | 1 007 960 | 5/1957 |
| DE | 2124684 | 11/1972 |
| DE | 89 09 492 | 3/1990 |
| DE | 41 00 422 | 7/1992 |
| FR | 2560052 | 8/1985 |

(List continued on next page.)

OTHER PUBLICATIONS

Cosman et al., "Methods of making nevous systems legions" *Neurosurgery*, Wilkins et al., Eds., McGraw–Hill Book Company, New York (1985) pp. 2490–2499.

Cosman et al., "Stereotactic radiofrequency lesion making" *Applied Neurophysiology* (1983) 46:160–166.

(List continued on next page.)

*Primary Examiner*—Lee Cohen
(74) *Attorney, Agent, or Firm*—Townsend and Townsend and Crew LLP

(57) ABSTRACT

A volumetric tissue ablation apparatus includes a probe having a plurality of wires journaled through a catheter with a proximal end connected to the active terminal of a generator and a distal end projecting from a distal end of the catheter. The probe wire distal ends are arranged in an array with the distal ends located generally radially and uniformly spaced-apart from the catheter distal end. A conductor connected to the return terminal of the generator is located relative to the probe wire array to form a closed electrical circuit through tissue to be ablated. Preferably, the probe wire array includes 10 wires, each formed in an arch from the catheter distal end. The conductor can be either a conventional ground plate upon which the tissue is supported, or a conductor wire extending through the probe and electrically insulated from the probe wires.

21 Claims, 10 Drawing Sheets

U.S. PATENT DOCUMENTS

| | | | |
|---|---|---|---|
| 4,011,872 A | 3/1977 | Komiya |
| 4,026,301 A | 5/1977 | Friedman et al. |
| 4,033,351 A | 7/1977 | Hetzel |
| 4,041,952 A | 8/1977 | Morrison, Jr. et al. |
| 4,326,888 A | 4/1982 | Frew |
| 4,353,371 A | 10/1982 | Cosman |
| 4,449,528 A | 5/1984 | Auth et al. |
| 4,474,179 A | 10/1984 | Koch |
| 4,492,231 A | 1/1985 | Auth |
| 4,511,356 A | 4/1985 | Froning et al. |
| 4,523,924 A | 6/1985 | Lacroix |
| 4,578,061 A | 3/1986 | Lemelson |
| 4,582,057 A | 4/1986 | Auth et al. |
| 4,655,216 A | 4/1987 | Tischer |
| 4,685,459 A | 8/1987 | Koch et al. |
| 4,691,703 A | 9/1987 | Auth et al. |
| 4,802,476 A | 2/1989 | Norenberg et al. |
| 4,819,633 A | 4/1989 | Bauer et al. |
| 4,823,791 A | 4/1989 | D'Amelio et al. |
| 4,936,842 A | 6/1990 | D'Amelio et al. |
| 4,938,761 A | 7/1990 | Ensslin |
| 4,974,595 A | 12/1990 | Norderstrom |
| 5,078,717 A | 1/1992 | Parins et al. |
| 5,083,565 A | 1/1992 | Parins |
| 5,089,002 A | 2/1992 | Kirwan, Jr. |
| 5,100,423 A | 3/1992 | Fearnot |
| 5,104,393 A | 4/1992 | Isner et al. |
| 5,259,394 A | 11/1993 | Bens |
| 5,281,216 A | 1/1994 | Klicek |
| 5,282,845 A | 2/1994 | Bush et al. |
| 5,322,503 A | 6/1994 | Desai |
| 5,354,279 A | 10/1994 | Hofling |
| 5,364,393 A | 11/1994 | Auth et al. |
| 5,366,490 A | 11/1994 | Edwards et al. |
| 5,370,675 A | 12/1994 | Edwards et al. |
| 5,380,319 A | 1/1995 | Saito et al. |
| 5,385,544 A | 1/1995 | Edwards et al. |
| 5,395,368 A | 3/1995 | Ellman et al. |
| 5,403,311 A | 4/1995 | Abele et al. |
| 5,433,739 A | 7/1995 | Sluijter |
| 5,458,597 A | 10/1995 | Edwards et al. |
| 5,470,308 A | 11/1995 | Edwards et al. |
| 5,472,441 A | 12/1995 | Edwards et al. |
| 5,486,161 A | 1/1996 | Lax et al. |
| 5,507,743 A | 4/1996 | Edwards et al. |
| 5,536,267 A | 7/1996 | Edwards et al. |
| 5,551,426 A | 9/1996 | Hummel et al. |
| 5,662,680 A | 9/1997 | Desai |
| 5,827,276 A | * 10/1998 | LeVeen et al. ............. 606/41 |
| 5,868,740 A | * 2/1999 | LeVeen et al. ............. 606/41 |

FOREIGN PATENT DOCUMENTS

| | | |
|---|---|---|
| GB | 2213381 | 8/1989 |
| JP | 63-275632 | 10/1988 |
| WO | US91/08388 | 11/1991 |
| WO | WO 93/08757 | 5/1993 |
| WO | WO 93/24066 | 12/1993 |
| WO | US94/01257 | 2/1994 |
| WO | US94/04550 | 5/1994 |
| WO | US94/04818 | 5/1994 |
| WO | US94/05141 | 5/1994 |
| WO | WO 94/26178 | 11/1994 |
| WO | WO 95/13113 | 5/1995 |
| WO | WO 95/13752 | 5/1995 |
| WO | WO 95/18575 | 7/1995 |
| WO | WO 96/04860 | 2/1996 |

OTHER PUBLICATIONS

Cosman et al., "Radiofrquency lesion generation and its effect on tissue impedance" *Applied Neurophysiology* (1988) 51:230–242.

Cragg et al., "Endovascular diathermic vessel occlusion" *Radiology* (1982) 144(2):303–308.

Sanchez et al., "Percutaneous tissue ablation by radiofrequency thermal energy as a prelim to tumour ablation" *Minimally Invasive Therapy* (1993) 2(6):299–305.

Tobler et al., "Improved outcome in the treatment of trigeminal neuralgia by percutaneous stereotactic rhizotomy with a new, curved tip electrode" *Neurosurgery* (1983) 12(3):313–317.

* cited by examiner

METHOD AND SYSTEMS FOR VOLUMETRIC TISSUE ABLATION

CROSS-REFERENCES TO RELATED APPLICATIONS

This application is a continuation-in-part of, and claims the benefit of priority from U.S. application Ser. No. 08/559,072, filed on Nov. 16, 1995, which is a continuation of U.S. application Ser. No. 08/410,344, filed on Mar. 24, 1995, now U.S. Pat. No. 5,868,740, issued on Feb. 9, 1999. The present application is also related to U.S. application Ser. No. 08/766,154, now U.S. Pat. No. 5,855,566 and U.S. application Ser. No. 08/764,058, now U.S. Pat. No. 5,827,276, and to U.S. application Ser. Nos. 09/500,705, and 09/500,732, both of which were filed on the same day as the present application. The full disclosures of each of these prior and co-pending applications are incorporated herein by reference.

TECHNICAL FIELD

The present invention relates generally to radio frequency electrodes for tissue ablation, and more particularly to an improved RF electrode having a spreading array of wires to ablate large volumes of tissue.

BACKGROUND OF THE INVENTION

The liver is a common repository for metastasis from many cancers, including those of the stomach, bowel, pancreas, kidney, and lung. In colorectal cancer the liver is the initial site of spread in more than one-third of patients, and is involved in more than two-thirds at the time of death. While patients with untreated colorectal metastasis to the liver have no five year survival, patients undergoing surgical resection have approximately a 25–30% five year survival. Unfortunately, only a limited number of patients are candidates for surgical resection.

Cryosurgery is also used for the treatment of hepatic metastasis. Cryosurgery, which relies on a freeze-thaw process to nonselectively kill cells, has been found equally effective as surgical resection but is more tissue sparing. While an improvement over open surgical tissue resection, cryosurgery still suffers from disadvantages. It is an open surgical procedure, requires placement of up to five relatively large probes, and can only be applied to a limited number of lesions. While percutaneous probes are being developed, they are currently capable only of treatment of smaller lesions. Typical lesions common to colorectal metastasis, however, are relatively large. Therefore, the outlook for percutaneous cryotherapy is guarded.

A number of investigators have used radio frequency hyperthermia with placement of external electrodes, for the treatment of liver cancers. Tumor cells are known to be more sensitive to heat than normal cells, and externally applied regional hyperthermia delivered with radio frequency tends to ablate the tumor while sparing the normal tissue of significant damage. While this therapy improves the response to systemic chemotherapy, it has uncertain benefit for long-term survival. One limitation of hyperthermia is that it is difficult to heat the tumors to a lethally high temperature. Moreover, tumor cells tend to become thermoresistant if they survive early treatments.

Percutaneous laser hyperthermia has also been used for primary and metastatic liver cancer. Laser fibers are introduced through needles, under ultrasound guidance. The lesions generated by laser are represented by hyperechoic foci on the real time ultrasound images, which can be used to monitor the size of the lesion. Low energy single fiber systems, which do not require a cooling system along the fiber, can generate areas of necrosis limited to approximately 15 mm diameter. Such small diameters are insufficient for the vast majority of lesions encountered clinically thus requiring multiple fiber placement and prolonged procedure times.

Radio frequency (RF) hyperthermia, using a standard electrosurgical generator and a fine needle partially sheathed in plastic, has also been proposed for the treatment of liver and other solid tumors. In one system, the apparatus was capable of generating lesions of approximately 1×2 cm in a pig liver. In order to produce larger treatment volumes with a single needle, high currents and temperatures have been employed, but produce charred and carbonized tissue, without enlarging the tissue volume being treated. To treat a larger lesion, multiple needle passes in different locations would be needed. In preliminary testing, this system established a 75% survival at 40 months.

It can therefore be seen that the treatment of primary and metastatic liver tumors and other solid tumors elsewhere in the body, remains problematic. Surgery is effective, but only a small percentage of affected patients are candidates. Cryotherapy has had improved results; but its applicable patient population is essentially the same as that for surgery. The percutaneous methods have the virtue of being less invasive, so they can be appropriately used for a larger spectrum of patients, but current percutaneous methods all suffer from a limited ability to ablate a large volume of tissue in a single procedure with a single probe passage.

SUMMARY OF THE INVENTION

It is therefore a general object of the present invention to provide an improved electrosurgical method and probe deployable in a percutaneous procedure that will produce a large volume of thermally ablated tissue with a single deployment.

It is a further object that such methods and probes should be useful in open surgical as well as percutaneous procedures.

Another object is to provide an electrosurgical probe which will provide uniformly treated tissue within a large volumetric lesion.

Still another object of the present invention is to provide a percutaneous electrosurgical probe which requires only a small access hole but provides for large volumetric tissue ablation.

Still another object is to provide an electrosurgical probe which avoids the problems of charring and carbonization common with single needle probes.

These and other objects will be apparent to those skilled in the art.

The present invention provides both methods and apparatus for the radio frequency (RF) treatment of a specific region within solid tissue, referred to hereinafter as a "treatment region." The methods and apparatus rely on introducing at least two electrodes, and usually at least three electrodes to a target site within the treatment region. After reaching the target site, the plurality of electrodes are deployed within the solid tissue, usually in a three-dimensional array and preferably in a configuration which conforms to or encompasses the entire volume of the treatment region, or as large a portion of the volume of the treatment region as possible. More preferably, the adjacent electrodes are evenly spaced-apart from each other (i.e., pairs of adjacent electrodes, will be spaced-apart in repeating pattern) so that application of RF current through the electrodes will result in generally uniform heating and necrosis of the entire tissue volume being treated. Advantageously, the use of multiple electrodes to treat a relatively large tissue volume allows the RF energy to be applied with a lower current density (i.e., from a larger total electrode area) and therefore at a lower temperature in the tissue immediately surrounding the electrode. Thus, charring and carbonization of tissue (which has heretofore been associated with the use of single electrode systems) is reduced. The uniform treatment of a large volume of tissue reduces the number of electrode deployments which are necessary for treating a tissue region of any given size.

In a first particular aspect, the method of the present invention comprises introducing at least two electrodes through solid tissue to a target site within a treatment region. The at least two electrodes are maintained in a radially constrained or collapsed configuration as they are advanced through the tissue to the target site and are then deployed from the target site further into the treatment region in a desired divergent pattern. RF current flow is then established between the at least two electrodes (i.e., bipolar) or among at least the two electrodes and a separate return electrode (i.e., monopolar). The monopolar return electrode will have a surface area which is sufficiently large to dissipate any electrosurgical effect. The at least two electrodes may be deployed by a variety of specific techniques. For example, a sheath may be initially placed using an obturator or stylet to the target site in a conventional manner. After removing the obturator or stylet, the electrodes can be introduced through the sheath and advanced from the distal end of the sheath into the solid tissue. Optionally, the electrodes may be disposed in or on an elongate member, such as a tube which reciprocatably receives the electrodes. The electrodes may then be advanced from the tube, or alternatively the tube may be withdrawn proximally from over the electrodes prior to advancement of the electrodes from the sheath into the tissue.

In a second specific aspect, the method of the present invention comprises advancing at least three electrodes from a target site within the treatment region. The electrodes diverge in a three-dimensional pattern, preferably with individual electrodes being evenly spaced-apart to provide for uniform volumetric treatment, as discussed above. Treatment is then performed by passing RF current among the at least three electrodes or between said three electrodes and a return electrode. Preferably, the method will employ more than three electrodes, often deploying at least five electrodes, preferably employing at least six electrodes, frequently employing at least eight electrodes, and often employing at least ten electrodes or more. It will be appreciated that a larger number of individual electrodes can enhance the uniformity of treatment while limiting the amount of power (current density) emitted from any single electrode, thus reducing the temperature in the immediate region of the electrode(s). Optionally, the at least three electrodes may be everted, i.e., turned first in a radially outward direction and then in a generally proximal direction, as they are advanced from the target site. The use of such multiple, everted electrodes provides a preferred array for treating relatively large tissue volumes. In particular, arrays of everted electrodes will provide current and heating in generally spherical volumes which will more closely match the spherical or ellipsoidal geometries of the typical tumor or other lesion to be treated. In contrast non-everted electrode arrays will often effect a conical or irregular treatment volume which may have less widespread applicability.

In a first aspect of the apparatus of the present invention, a probe system comprises an elongate member having a proximal end and a distal end. At least two solid-tissue-penetrating electrode elements are reciprocatably disposed on or in the elongate member so that they may be advanced into tissue after the elongate member has been introduced through solid tissue to a target site in or near the treatment region. A means for introducing the elongate member through tissue to the target site is also provided. The means may take a variety of forms, including a sheath and obturator (stylet) assembly which may be used to provide the initial penetration. Alternatively, a self-penetrating element may be provided directly on the elongate member. Other conventional devices and techniques of the type used for introducing shafts and other elongate members to solid tissue may also be employed.

The tissue-penetrating electrode elements may comprise wires which are received within an axial lumen of the elongate member. For example, the wires may be bundled together over a proximal portion thereof, but remain separate and shaped over their distal portion so that they diverge in a selected pattern when advanced into tissue. Usually, the wires will be advanced directly from the elongate member (when the elongate member is left inside the sheath or the sheath is withdrawn), but could alternatively be advanced from the sheath when the elongate member is withdrawn proximally from over the electrodes prior to penetration of the electrodes into the tissue.

In a second aspect of the apparatus of the present invention, a probe system comprises an elongate member having a proximal end and a distal end, and at least three solid-tissue penetrating electrode elements reciprocatably attached to the elongate member. The at least three electrodes are configured to diverge in a three-dimensional pattern as they are advanced in a distal direction from the elongate member. Usually, the elongate member is a tube having an axial lumen which reciprocatably receives the tissue-penetrating electrode element, and the electrode elements comprise individual wires which may be bundled as described above. The distal ends of the wires or other electrode elements are preferably shaped so that they will assume a radially constrained configuration while present in the axial lumen of the tube and will assume a radially divergent configuration when axially extended from the tube. In a preferred configuration, the distal ends of at least some of the wires are shaped so that they assume outwardly everted configuration as they are axially extended from the tube or other elongate member. The probe system may include one, two, or more groups of at least three electrodes which are axially spaced-apart from each other. In particular, such axially spaced-apart groups of electrodes may extend from the distal end of the elongate member or may be distributed along the elongate member and individually extendable to assume the desired three-dimensional configuration. Preferably, each group of tissue-penetrating wires or other electrode elements will include more than three electrodes, as described generally above.

GENERAL DESCRIPTION OF THE SYSTEM OF THE PRESENT INVENTION

Figure 2:
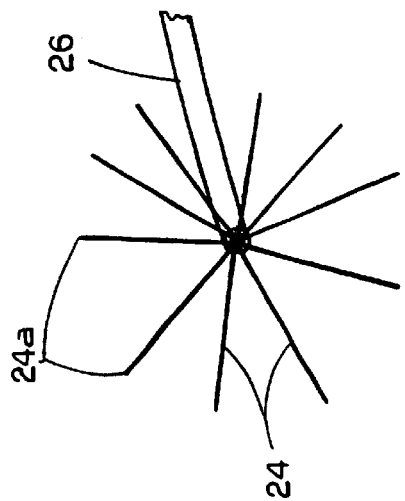
FIG. 2 is an end view of the apparatus of FIG. 1.

Systems according to the present invention will be designed to introduce a plurality of electrode elements to a treatment region within patient solid tissue. The treatment region may be located anywhere in the body where hypothermic exposure may be beneficial. Most commonly, the treatment region will comprise a solid tumor within an organ of the body, such as the liver, kidney, pancreas, breast, prostate (not accessed via the urethra), and the like. The volume to be treated will depend on the size of the tumor or other lesion, typically having a total volume from 1 $cm^3$ to 150 $cm^3$, usually from 1 $cm^3$ to 50 $cm^3$, and often from 2 $cm^2$ to 35 $cm^2$. The peripheral dimensions of the treatment region may be regular, e.g., spherical or ellipsoidal, but will more usually be irregular. The treatment region may be identified using conventional imaging techniques capable of elucidating a target tissue, e.g., tumor tissue, such as ultrasonic scanning, magnetic resonance imaging (MRI), computer-assisted tomography (CAT), fluoroscopy, nuclear scanning (using radiolabeled tumor-specific probes), and the like. Preferred is the use of high resolution ultrasound which can be employed to monitor the size and location of the tumor or other lesion being treated, either intraoperatively or externally.

Systems according to the present invention will employ a plurality of tissue-penetrating electrodes, typically in the form of sharpened, small diameter metal wires which can penetrate into tissue as they are advanced from a target site within the treatment region, as described in more detail hereinafter. The electrode elements, however, can also be formed in other manners, such as blades, helices, screws, and the like. The primary requirement of such electrode elements is that they can be deployed in an array, preferably a three-dimensional array, emanating generally from a target site within the treatment region of the tissue. Generally, the electrode elements will be first introduced to the target site in a radially collapsed or other constrained configuration, and thereafter advanced into the tissue from a delivery element in a divergent pattern to achieve the desired three-dimensional array. Preferably, the electrode elements will diverge radially outwardly from the delivery element (located at the target site) in a uniform pattern, i.e., with the spacing between adjacent electrodes diverging in a substantially uniform and/or symmetric pattern. In the exemplary embodiments, pairs of adjacent electrodes will be spaced-apart from each other in similar or identical, repeated patterns and will usually be symmetrically positioned about an axis of the delivery element. The electrode elements may extend or project along generally straight lines from the target site, but will more usually be shaped to curve radially outwardly and optionally to evert proximally so that they face partially or fully in the proximal direction when fully deployed. It will be appreciated that a wide variety of particular patterns can be provided to uniformly cover the region to be treated.

A preferred form of the individual electrode element of an electrode array is a single wire having a shaped distal portion which can be extended from the delivery element at the target site in the tissue to diverge in a desired pattern. Such wires can be formed from conductive metals having a suitable shape memory, such as stainless steel, nickel-titanium alloys, spring steel alloys, and the like. The wires may have circular or non-circular cross-sections, with circular wires typically having a diameter in the range from about 0.1 mm to 2 mm, preferably from 0.2 mm to 0.5 mm, often from 0.2 mm to 0.3 mm. The non-circular wires will usually have equivalent cross-sectional areas. Optionally, the distal ends of the wires may be honed or sharpened to facilitate their ability to penetrate tissue. The distal ends of such wires may be hardened using conventional heat treatment or other metallurgical processes. Such wires may be partially covered with insulation, although they will be at least partially free from insulation over their distal portions which will penetrate into the tissue to be treated. In the case of bipolar electrode arrays, it will be necessary to insulate the positive and negative electrode wires in any regions where they would be in contact with each other during the power delivery phase. In the case of monopolar arrays, it may be possible to bundle the wires together with their proximal portions having only a single layer of insulation over the entire bundle. Such bundled wires may be brought out directly to a suitable RF power supply, or may alternatively be connected via other (intermediate) electrical conductors, such as coaxial cable, or the like.

The above-described electrode characteristics apply only to active electrodes intended to have the desired surgical effect, i.e., heating of the surrounding tissue. It will be appreciated that in monopolar operation, a passive or dispersive "electrode" must also be provided to complete the return path for the circuit being created. Such electrodes, which will usually be attached externally to the patient's skin, will have a much larger area, typically about 130 $cm^2$ for an adult, so that current flux is sufficiently law to avoid significant heating and other surgical effects. It may also be possible to provide such a dispersive return electrode directly on a portion of a sheath or elongate member of the system of the present invention, as described in more detail below (generally, when the return electrode is on the sheath, the device will still be referred to as bipolar).

The RF power supply may be a conventional general purpose electrosurgical power supply operating at a frequency in the range from 400 kHz to 1.2 MHz, with a conventional sinusoidal or non-sinusoidal wave form. Such power supplies are available from many commercial suppliers, such as Valleylabs, Aspen, Bovie, and Birtcher.

The plurality of electrode elements will usually be contained by or within an elongate member which incorporates the delivery element, typically a rigid, metal or plastic cannula. The elongate member serves to constrain the individual electrode elements in a radially collapsed configuration to facilitate their introduction to the tissue target site. The electrode elements can then be deployed to their desired configuration, usually a three-dimensional configuration, by extending distal ends of the electrode elements from the elongate member into the tissue. In the case of the tubular cannula, this can be accomplished simply by advancing the distal ends of the electrode elements distally forward from the tube so that they emerge and deflect (usually as a result of their own spring memory) in a radially outward pattern. Alternatively, some deflection element or mechanism could be provided on the elongate member to deflect members with or without shape memory in a desired three-dimensional pattern.

A component or element will be provided for introducing the elongate member to the target site within the treatment region to be treated. For example, a conventional sheath and sharpened obturator (stylet) assembly can be used to initially access the target site. The assembly can be positioned under ultrasonic or other conventional imaging, with the obturator/stylet then being removed to leave an access lumen through the sheath. The electrode elements can then be introduced through the sheath lumen, typically while constrained in the elongate member. The electrode elements are then extended distally beyond the distal end of the sheath into the treatment region of tissue, and the elongate member can subsequently be withdrawn or left in place. RF current can then be applied through the electrodes in either a monopolar or bipolar fashion. With monopolar treatment, a dispersive plate attached externally to the patient is attached to the other lead from the RF power supply. Alternatively, a return electrode having a relatively large surface area can be provided on the elongate member, or the sheath. In bipolar operation, the individual electrode elements can be connected alternately to the two poles of the RF power supply. Alternatively, one or more additional electrode elements can be penetrated into the tissue and serve as a common electrode connected at the second pole.

DESCRIPTION OF THE SPECIFIC EMBODIMENTS

Figure 1:
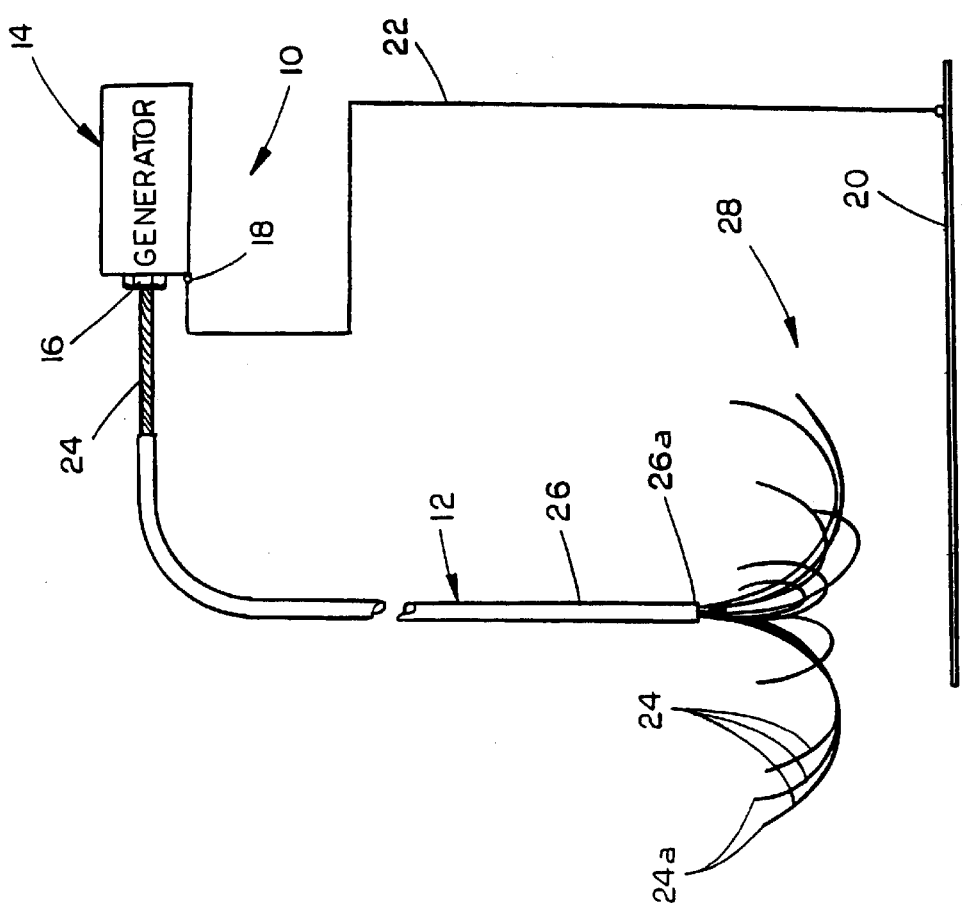
FIG. 1 is a side elevational view of the tissue ablation apparatus of the present invention.

Referring now to the drawings, in which similar or corresponding parts are identified with the same reference numeral, and more particularly to FIG. 1, the volumetric tissue ablation apparatus of the present invention is designated generally at 10 and includes a probe 12 electrically connected to a generator 14.

In experiments with a prototype of the present invention, the inventor utilized a Bovie® X-10 electrosurgical unit for generator 14, to generate radio frequency current at specific energies, using the probe 12 as the active electrode and placing the tissue sample on a dispersive or ground plate. Thus, generator 14 includes at least an active terminal 16 and a return terminal 18, with a dispersive or ground plate 20 electrically connected by conductor 22 to terminal 18.

Probe 12 is comprised of a plurality of electrically conductive wires 24 which are bundled at a proximal end and connected to terminal 16 to conduct RF current therefrom. Wires 24 are threaded through an electrically insulated or non-conductive tube or catheter 26.

Wires 24 are preferably formed of spring wire or other material which will retain memory. As shown in FIG. 1, a 10-wire array 28 is formed with each wire 24 arching from catheter 26 in a general "U" shape with each wire substantially uniformly separated, as shown in FIG. 2. Thus, array 28 is formed of a plurality of wires 24 curving radially outwardly from the axis of distal end 26a of catheter 26. Wires 24 all extend a length such that a portion of each wire 24 is perpendicular to the axis of tube 26, and preferably continue curving rearwardly back upon themselves such that wire distal ends 24a are oriented generally parallel to the axis of the tube distal end 26a. As shown in FIG. 1, wire distal ends 24a generally lay within a plane orthogonal to the tube distal end 26a, and uniformly spaced-apart from one another.

Because wires 24 are formed of spring steel, they may be drawn within catheter 26, for percutaneous insertion. Once distal end 26a of catheter 26 is in position, sliding wires 24 through catheter 26 will permit the memory of the wires to take the radially disposed shape of the array 28 shown in FIGS. 1 and 2.

Figure 3:
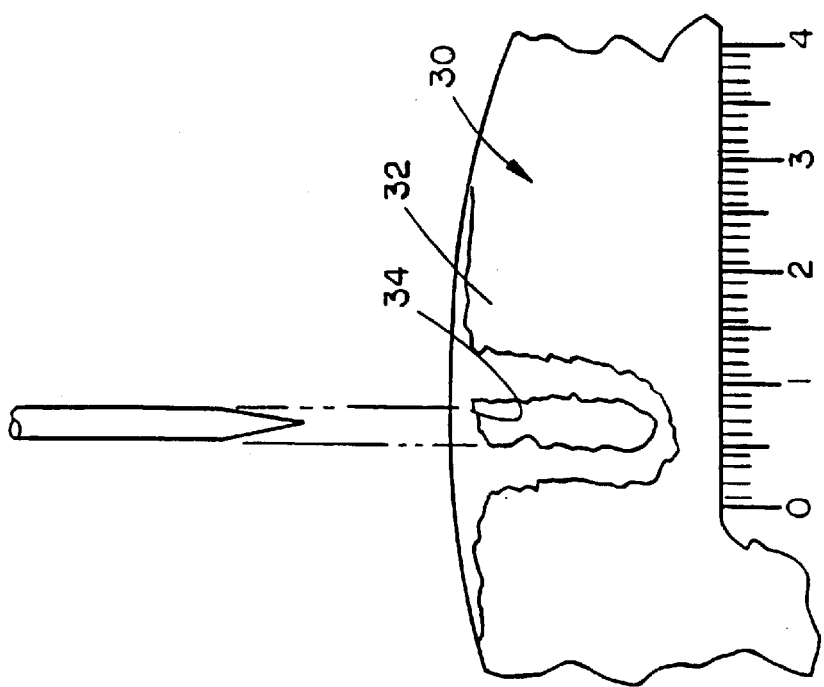
FIG. 3 is a sectional view through tissue, showing the prior art affects of a single needle probe.

FIG. 3 is a sectional view taken through a liver sample 30, showing the results of a prior art 18 gauge straight needle 31 with 1.2 cm of exposed metal when inserted in liver 30 and operated at 20 watts of power, with 100% coagulation current, for a period of 5 minutes. As can be seen in FIG. 3, the lesion 32 produced by the single needle has a narrow elliptical (nearly cylindrical) shape with a diameter of approximately 1.2 cm and a length of approximately 2 cm. FIG. 3 also shows the effects of very high temperatures near the probe tip with gas formation common with single needle electrosurgical sources, resulting in charred and carbonized tissue 34 immediately around the needle. The charring and associated gas formation at the site of the single needle probes significantly limits the power which may be applied.

Figure 4:
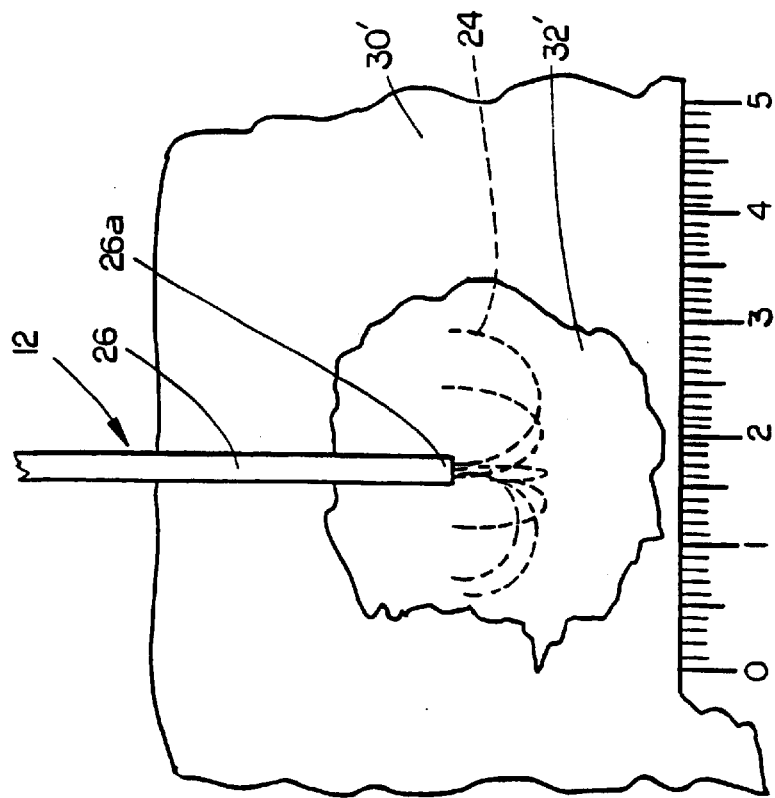
FIG. 4 is a sectional view through tissue showing the results of the probe of the present invention.

FIG. 4 is a sectional view through a liver sample 30' showing the necrotic lesion 32' produced by the 10 wire array 28 of probe 12 of the present invention. Probe 12 is located in tissue sample 30' with tube distal end 26a positioned generally centrally at the site at which a lesion is desired. Various methods, known in the art, may be utilized to position probe 12, prior to deployment of wires 24 (shown deployed in hidden lines). Preferably, positioning of tube distal end 26a is confirmed by ultrasound or other imaging techniques. Once tube 26 is appropriately positioned, wires 24 are deployed into tissue 30', the memory of the wire material causing the wire deployment to take a predetermined array shape.

The applicants utilized the same generator 14 at a power of 60 watts, with 100% coagulation current, for a period of 5 minutes. It can be seen that the necrotic lesion produced by probe 12 is roughly spherical in shape and has a diameter of approximately 3.5 cm. Furthermore, there is no charring evident, indicating no sparking, and a more uniform temperature distribution within the volume of tissue being treated. During testing, it was found that the temperature of the tissue 2 cm away from the access of probe 12 at the end of the 5 minutes was 51.4° C. The same 10 wire probe 12 was used repeatedly at the same settings and produced substantially identical lesions. It was also found that the area of lethal heating may extend at least another centimeter beyond the visible lesion shown in FIG. 4, after thermistor measurements were taken during repeated experiments with probe 12.

Figure 5:
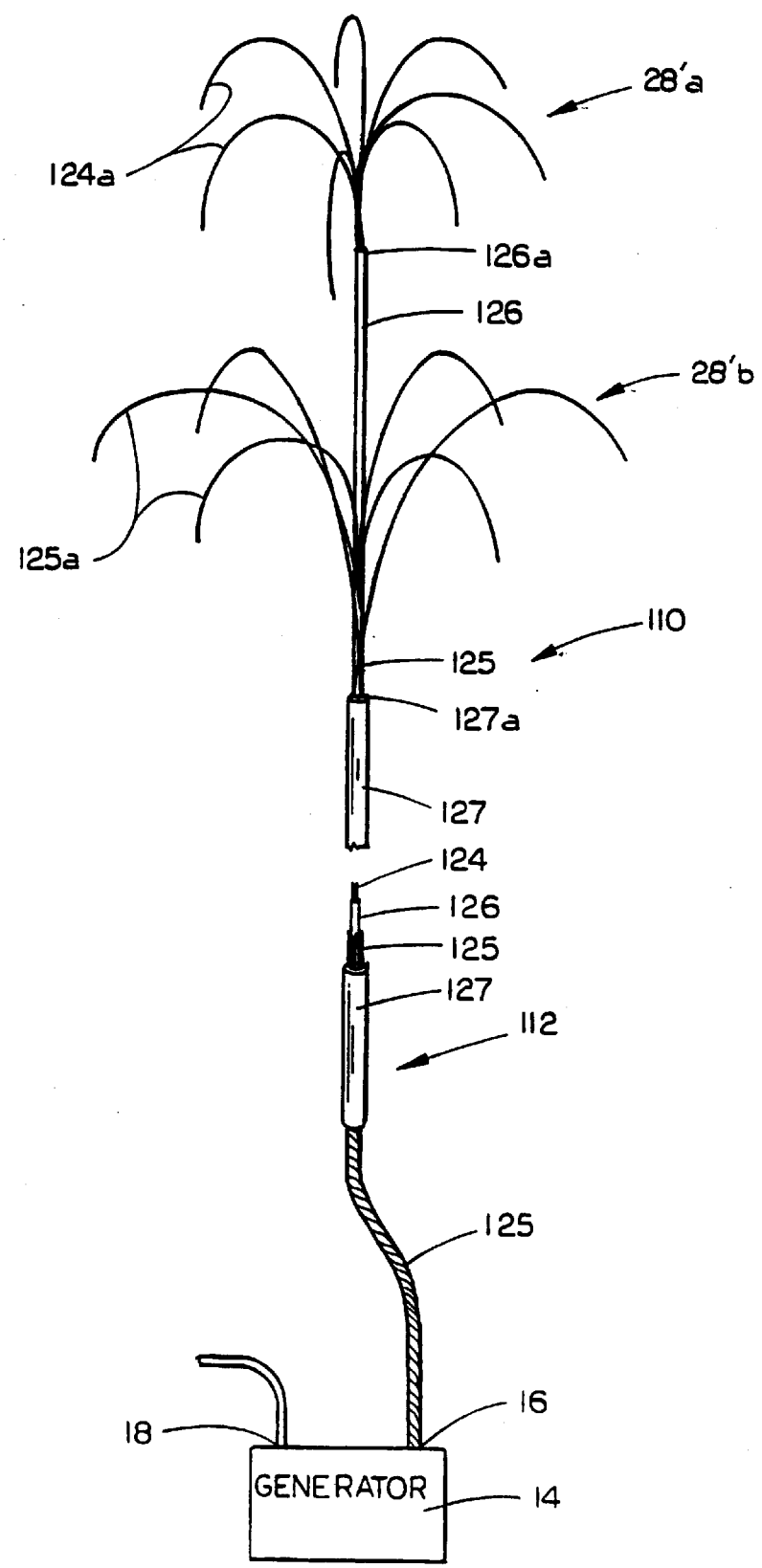
FIG. 5 is a side perspective view of a second embodiment of the probe of the present invention.

While FIGS. 1 and 2 show a general "fountain" shaped array 28 with 10 wires 24, various other array designs are equally suitable, utilizing uniform spacing of the wire distal ends 24a from catheter distal end 26a to produce a symmetrical lesion, or with non-uniform spacing to produce an asymmetric lesion. For example, as shown in FIG. 5, multiple arrays 28' may be formed spaced longitudinally from one another. This embodiment of the monopolar tissue ablation apparatus is designated generally at 110 and includes a probe 112 electrically connected to generator 14. Probe 112 includes a first wire bundle 124 journaled through a tube 126 with wire distal ends 124a deployable to form a first array 28'a extending from tube distal end 126a. A second wire bundle 125 surrounds tube 126 within an outer tube 127, with wire distal ends 125a deployable to form a second array 28'b projecting from outer tube distal end 127a. The proximal ends 124b and 125b of wire bundles 124 and 125 are electrically connected in common to active terminal 16.

In operation, outer tube 127 is positioned with distal end 127a located at the predetermined site for the lesion. The second array 28'b is then formed by deploying wire ends 125a of second wire bundle 125. Inner tube 126 is then moved axially such that tube distal end 126a is spaced longitudinally from tube distal end 127a. First wire bundle 124 is then deployed such that wire ends 124a form array 28'a longitudinally spaced from array 28'b.

Figure 6:
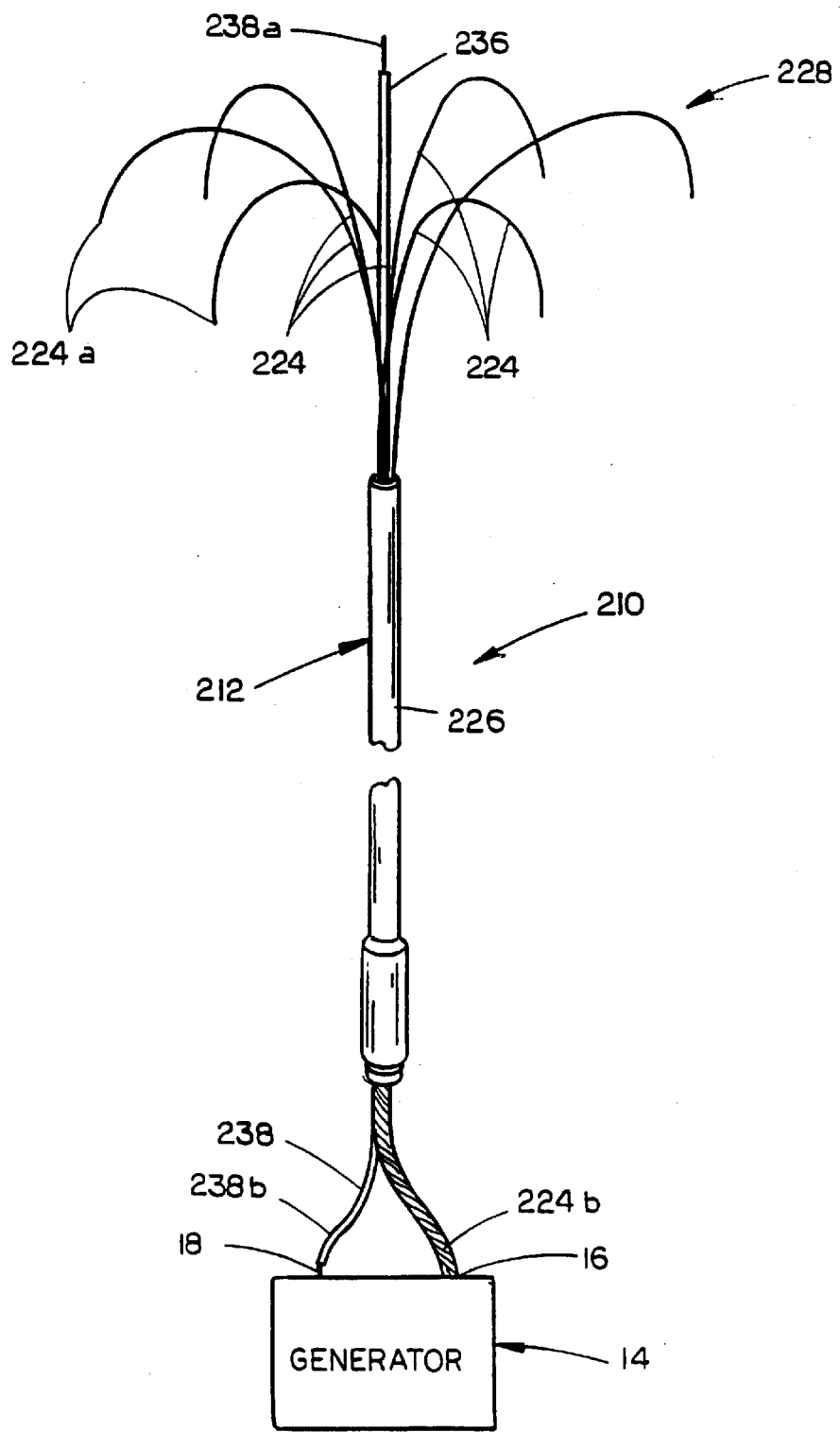
FIG. 6 is a side perspective view of a bipolar embodiment of the invention.

Referring now to FIG. 6, a bipolar embodiment of the tissue ablation apparatus is designated generally at 210 and includes a probe 212 electrically connected to a generator 14. Wires 224 are electrically connected to terminal 16 on generator 14 and terminate distally in an array 228 in the same fashion as the array 28 of the first embodiment. However, apparatus 210 includes an integral return path consisting of a return wire 238 coated with an electrically nonconductive material 236, which extends through catheter 226 within the bundle of wires 224, and has a distal end 238a projecting generally centrally within array 228. The proximal end 238b of wire 238 is connected to return terminal 18, to provide an electrical circuit when probe 212 is deployed within tissue. Thus, a dispersive plate is unnecessary.

Figure 7:
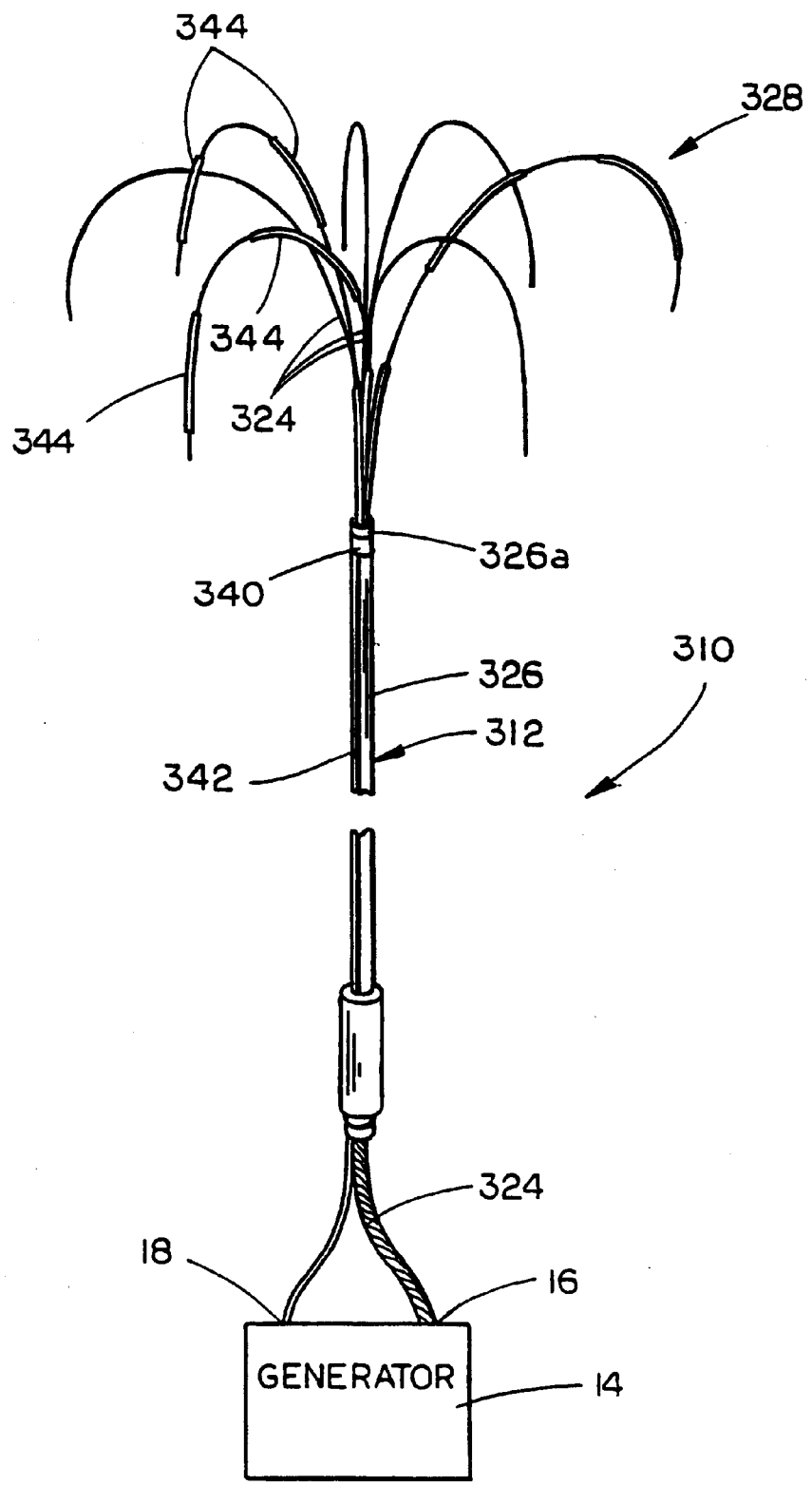
FIG. 7 is a side perspective view of a second bipolar probe.

Referring now to FIG. 7, a second bipolar embodiment of the tissue ablation apparatus is designated generally at 310 and includes a probe 312 with wires 324 connected to active terminal 16 of generator 14. Wires 324 project from distal end 326a of tube 326 to form an array 328.

Bipolar apparatus 310 differs from bipolar apparatus 210 of FIG. 6, in two ways. First, a collar 340 is attached to the exterior of tube distal end 326a and is electrically connected to return terminal 18 by a conductor 342, to form an electrical return for current supplied by wires 324. Conductor 342 may be affixed to the outside of tube 326, or threaded through tube 326 while electrically insulted from wires 324.

Second, wires 324 have portions 344 which are coated with an electrically insulative material. Portions 344 are spaced-apart along a plurality of wires 324 in order to restrict current flow from selected portions of wires 324 in order to create a more uniform distribution of heat from the remaining exposed portions of wires 324.

Figure 8:
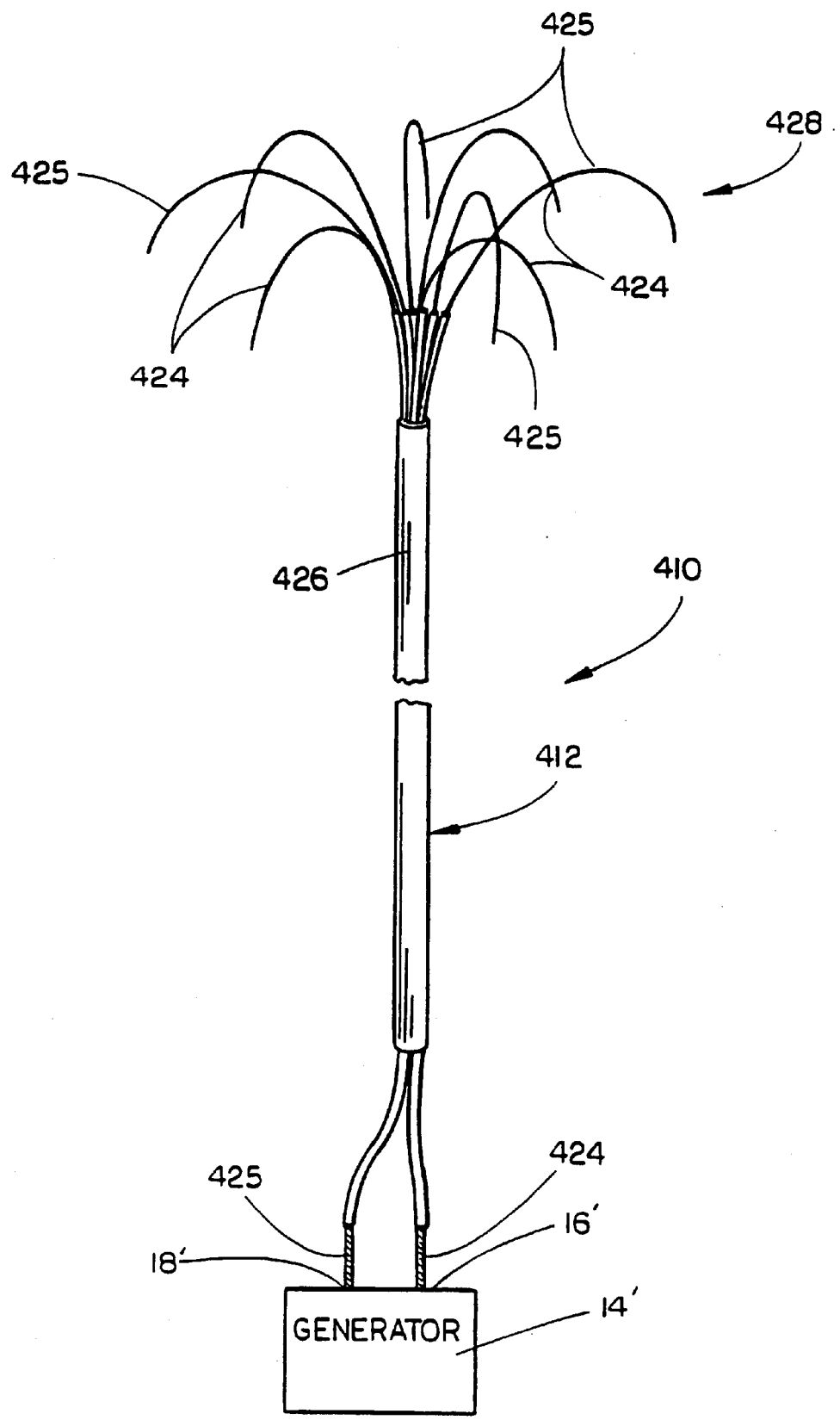
FIG. 8 is a side perspective view of a third bipolar probe.

A third bipolar embodiment of the tissue ablation apparatus is designated generally at 410 in FIG. 8. Bipolar apparatus 410 includes a probe 412 with one set of wires 424 connected to one terminal 16' of a current generator 14', and a second set of wires 425 connected to the opposite terminal 18'. The individual wires of wire bundles 424 and 425 have an electrically insulative coating through tube 426, to prevent electrical contact with one another. Wires 424 and 425 preferably alternate throughout array 428, such that current flows between wires 424 and wires 425.

DESCRIPTION OF THE METHOD OF THE PRESENT INVENTION

Figure 9:
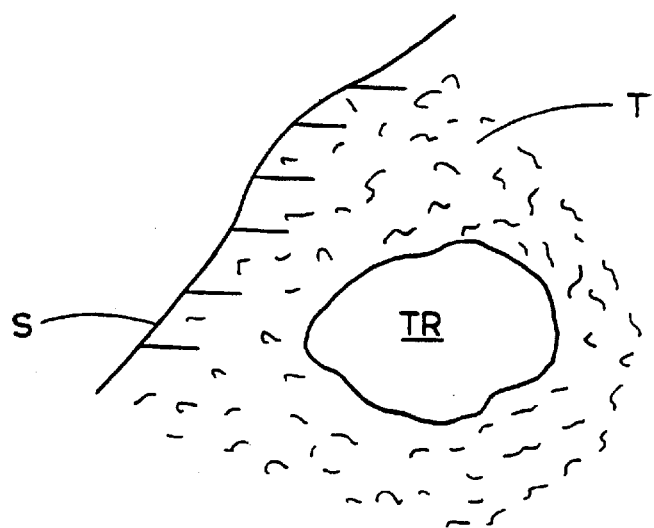
FIGS. 9–14 illustrate use of an exemplary probe system according to the present invention in RF treatment of a target region of solid tissue.

Referring now to FIGS. 9–14, a treatment region TR within tissue T is located beneath the skin S of a patient. The treatment region may be a solid tumor or other lesion where it is desired to treat the region by RF hyperthermia. The treatment region TR prior to treatment is shown in FIG. 9.

Figure 10:
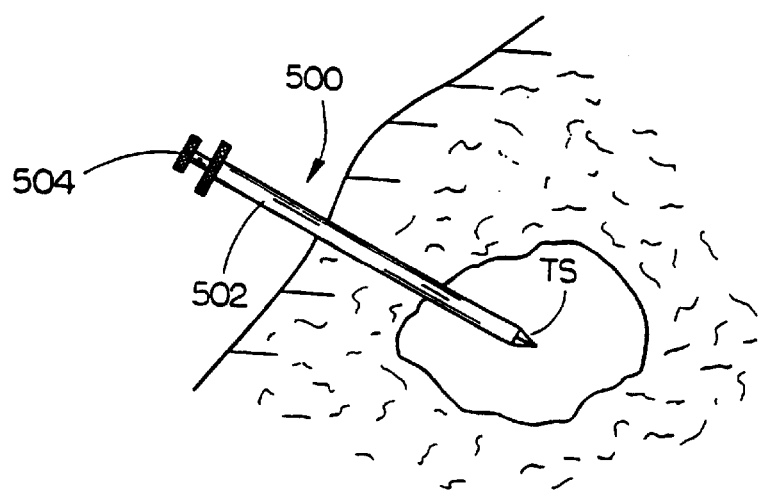
Figure 11:
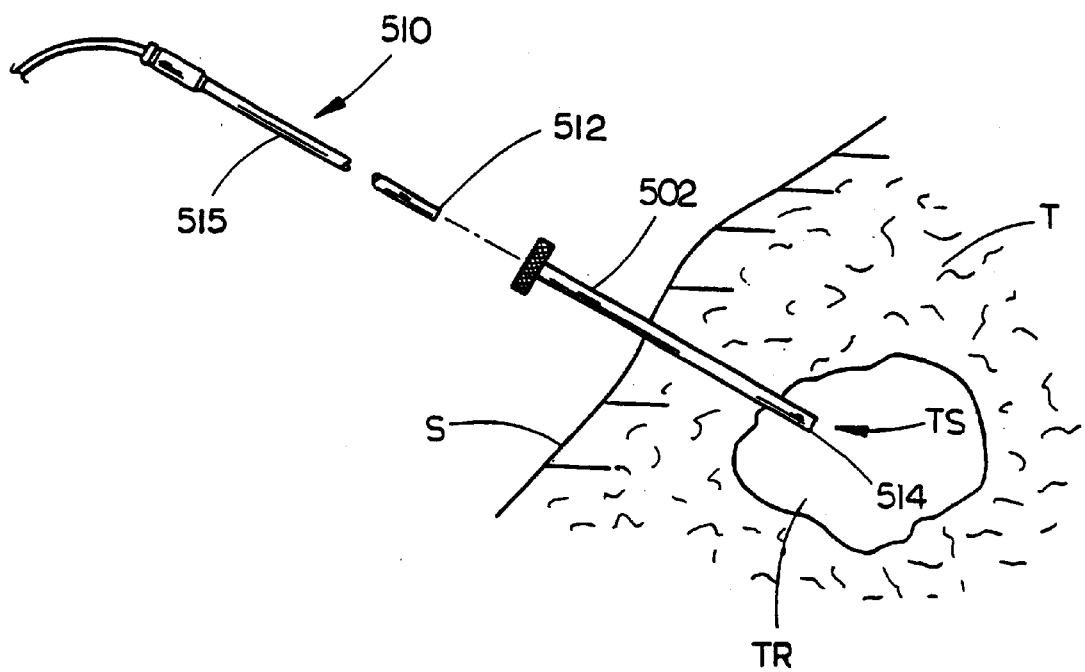
Figure 12:
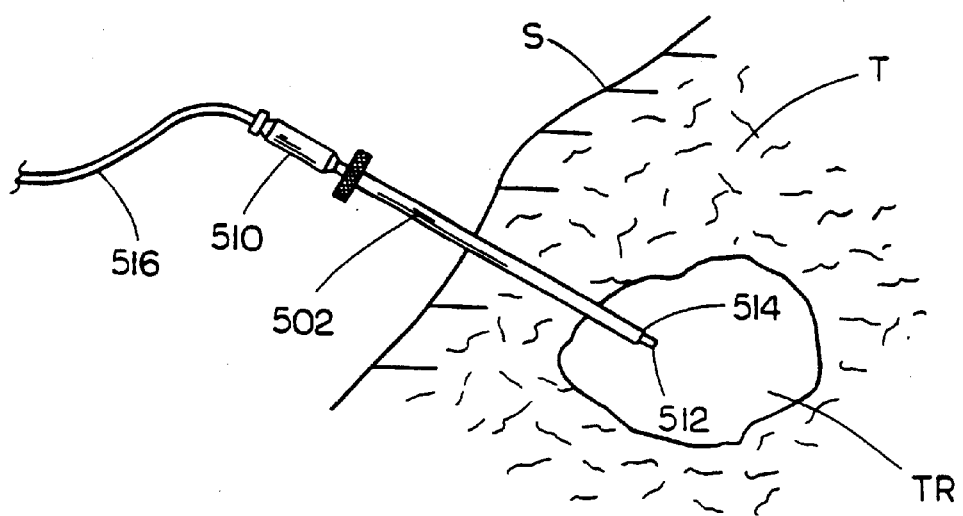
Figure 13:
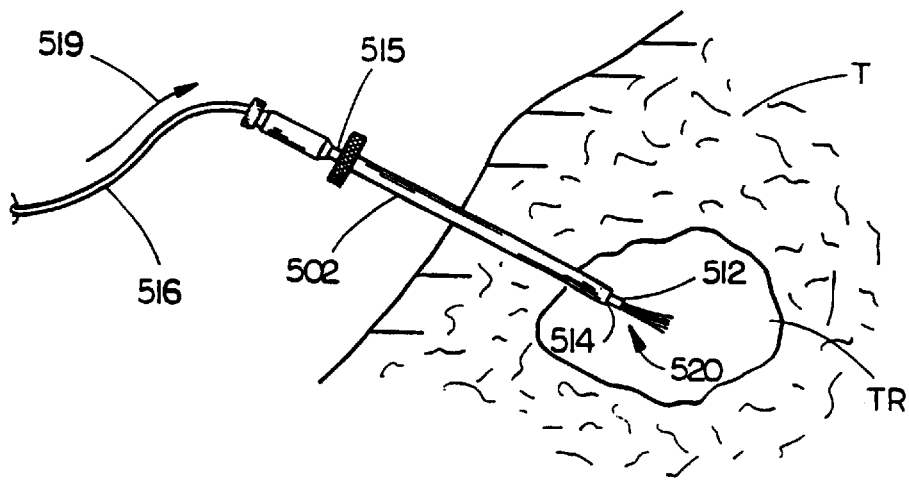
Figure 14:
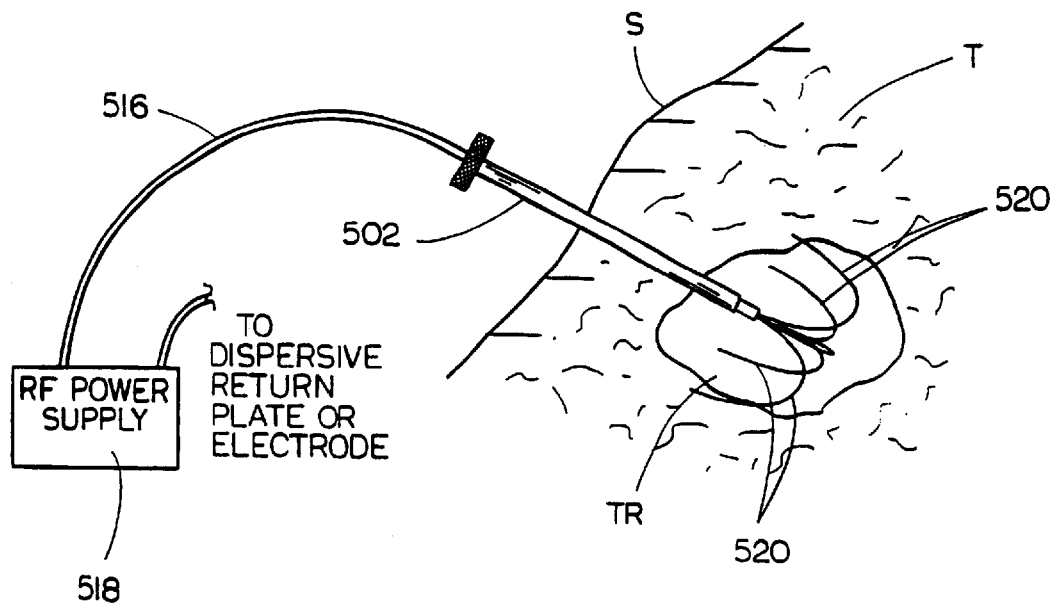

In order to introduce an electrode array according to the method of the present invention, a conventional sheath and obturator/stylet assembly 500 is introduced percutaneously (through the skin) so that a distal end of the sheath lies at or within a target site TS, as shown in FIG. 10. Obturator/stylet 504 is then withdrawn from sheath 502, leaving an access lumen to the target site, as shown in FIG. 11. A delivery probe 510 incorporating the features of the present invention is then introduced through the access lumen of the sheath 502 so that a distal end 512 of an outer cannula 515 of the probe lies near the distal end 514 of the sheath 502, as shown in FIG. 12. Individual electrodes 520 are then extended distally from the distal end 512 of the probe 510 by advancing cable 516 in the direction of arrow 519, as shown in FIG. 13. The electrodes 520 are advanced so that they first diverge radially outwardly from each other (FIG. 13), eventually everting backward in the proximal direction, as shown in FIG. 14. If desired, the cannula 515 of probe 510 is then withdrawn proximally over electrode cable 516, and the electrode cable is then attached to an RF power supply 518 in a monopolar manner, also as shown in FIG. 14. Radio frequency current may then be applied from the power supply 518 at a level and for a duration sufficient to raise the temperature of the treatment region TR by a desired amount, typically to a temperature of at least 42° C., usually to at least 50° C., for 10 minutes or longer. Higher temperatures will generally require much shorter treatment times.

Figure 15:
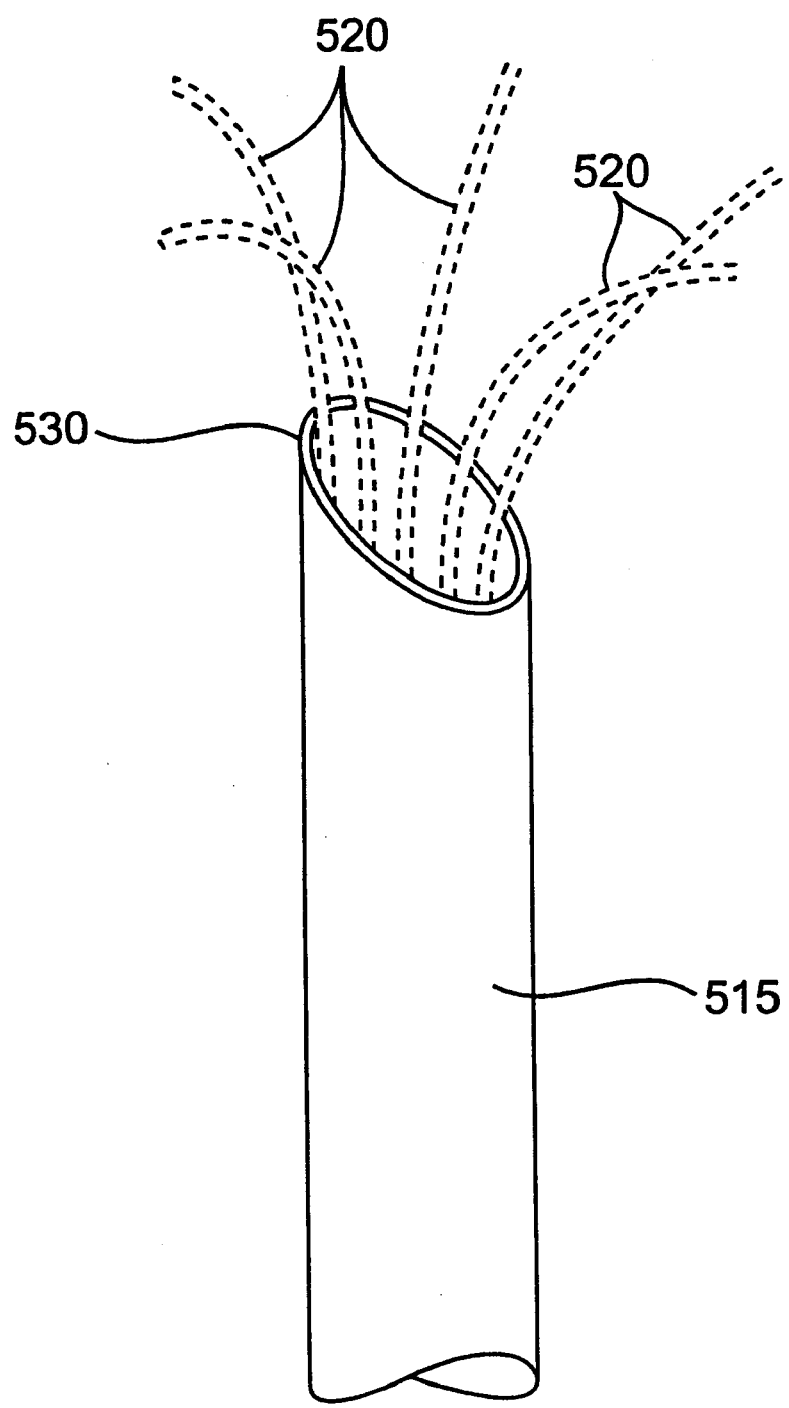
FIG. 15 illustrates an elongate member having a sharp tip which acts as a self-penetrating element to enhance tissue penetration.

While the method and system just described employs a separate sheath and obturator/stylet assembly 500 for introducing the treatment electrodes, it will be appreciated that the use of such a separate introducer is not necessary. Alternatively, the electrodes could be introduced through the elongate member, where the elongate member is provided with a self-penetrating element, such as a sharp tip 330 (FIG. 15) or an electrosurgical tip, to enhance tissue penetration. As a further alternative, a bundle of electrodes could be introduced in any constrained fashion (e.g., a removable ring, soluble sheath, etc.) with the constraint selectively released after they have reached the target site within the treatment region. The present invention thus will encompass use of a variety of specific systems for introducing a plurality of electrodes to the target site in solid tissue, and thereafter releasing and diverging the individual electrode elements into a treatment region surrounding the target site in a desired three-dimensional array or other configuration or geometry.

Whereas the invention has been shown and described in connection with the preferred embodiments thereof, many modifications, substitutions and additions may be made which are within the intended broad scope of the appended claims. It can therefore be seen that the volumetric tissue ablation apparatus of the present invention provides an effective and desirable electrosurgical ablation system which is suitable for percutaneous and open surgical introduction, produces uniform lesions, and produces lesions large enough to treat a large spectrum of patients.

What is claimed is:

1. A method for treating a treatment region within solid tissue of a patient with radio frequency current, said method comprising:

introducing at least three electrodes in a distal direction through tissue to a site within solid tissue proximate the treatment region, wherein said electrodes remain radially constrained while being introduced;

advancing said at least three electrodes distally from the site within solid tissue, wherein said electrodes diverge radially outwardly in a three-dimensional pattern as they are advanced through solid tissue; and establishing radio frequency current flow among the at least three electrodes.

2. A method as in claim 1, wherein advancing at least three electrodes having distal ends which are shaped so that they assume outwardly everting configurations as they are distally advanced.

3. A method as in either claim 1 or 2, wherein advancing comprises advancing at least five electrodes.

4. A method as in claim 3, wherein advancing comprises advancing at least six electrodes.

5. A method as in claim 4, wherein advancing comprises advancing at least eight electrodes.

6. A method as in claim 1 or 2, wherein advancing comprises advancing the electrodes so that spacing between adjacent electrodes is similar so that the electrodes are positioned symmetrically about an axis.

7. A method as in claim 3, wherein advancing comprises advancing the electrodes so that spacing between adjacent electrodes is similar so that the electrodes are positioned symmetrically about an axis.

8. A method as in claim 4, wherein advancing comprises advancing the electrodes so that spacing between adjacent electrodes is similar so that tile electrodes are positioned symmetrically about an axis.

9. A method as in claim 5, wherein advancing comprises advancing the electrodes so that spacing between adjacent electrodes is similar so that the electrodes are positioned symmetrically about an axis.

10. A method as in claim 1, wherein the electrodes evert as they are advanced distally from the site.

11. A method as in claim 10, wherein the electrodes fully evert.

12. A method as in claim 1, wherein establishing radio frequency current flow among the at least three electrodes comprises establishing radio frequency current flow among the at least three electrodes and a dispersive plate positioned remotely from the at least three electrodes.

13. A method as in claim 1, wherein the solid tissue comprises liver tissue.

14. A probe system for penetrating a plurality of electrodes into solid tissue, said probe system comprising:

a rigid cannula having a proximal end and a distal end;

a self-penetrating element on the cannula to enhance tissue penetration; and a plurality of at least three electrode elements radially constrained within the cannula, wherein the electrode elements can be advanced distally forward from the distal end of the cannula so that the electrode elements emerge and deflect as a result of their own spring memory in a radially outward pattern, wherein the electrode elements curve radially outwardly as they are advanced.

15. A probe system as in claim 14, wherein the self-penetrating element is a sharp tip at the distal end of the rigid cannula.

16. A probe system as in claim 14, wherein the plurality includes at least five electrode elements.

17. A probe system as in claim 14, wherein the plurality includes at least eight electrode elements.

18. A probe system as in claim 14, wherein the plurality includes at least ten electrode elements.

19. A probe system as in claim 14, wherein the electrode elements evert proximally when fully deployed.

20. A probe system as in claim 14, wherein the electrode elements are uniformly spaced from each other as they are advanced from the cannula.

21. A probe system as in claim 20, wherein the electrode elements evert proximally when fully deployed.

* * * * *

UNITED STATES PATENT AND TRADEMARK OFFICE
CERTIFICATE OF CORRECTION

PATENT NO. : 6,575,967 B1
DATED : June 10, 2003
INVENTOR(S) : Robert F. Leveen and Randy Fox It is certified that error appears in the above-identified patent and that said Letters Patent is hereby corrected as shown below:

Column 10,
Line 53, remove "in a distal direction"
Line 57, add -- generally -- between "electrodes" and "distally"
Line 58, add -- distal ends of -- between "wherein" and "said"
Line 60, remove "they"
Line 60, add -- said electrodes -- before "are"
Lines 61 and 62, replace "among the at least three electrodes" with -- between said at least three electrodes and a dispersive electrode -
Line 63, replace "advancing at least three electrodes having" with -- said --
Line 64, remove "which"

Signed and Sealed this

Twenty-ninth Day of June, 2004

JON W. DUDAS
*Acting Director of the United States Patent and Trademark Office*